(12) United States Patent
Nederlof

(10) Patent No.: US 9,159,531 B2
(45) Date of Patent: Oct. 13, 2015

(54) SAMPLE CARRIER FOR AN ELECTRON MICROSCOPE

(71) Applicant: FEI Company, Hillsboro, OR (US)

(72) Inventor: Frank Nederlof, Nuenen (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/154,753

(22) Filed: Jan. 14, 2014

(65) Prior Publication Data

US 2014/0197311 A1 Jul. 17, 2014

Related U.S. Application Data

(60) Provisional application No. 61/752,514, filed on Jan. 15, 2013.

(30) Foreign Application Priority Data

Jan. 15, 2013 (EP) ..................................... 13151244

(51) Int. Cl.
*H01J 37/20* (2006.01)
*G01N 23/22* (2006.01)
*G01N 23/225* (2006.01)

(52) U.S. Cl.
CPC ............ *H01J 37/20* (2013.01); *G01N 23/2204* (2013.01); *G01N 23/2251* (2013.01); *H01J 2237/201* (2013.01); *H01J 2237/26* (2013.01)

(58) Field of Classification Search
CPC ... H01J 37/20; H01J 37/26; H01J 2237/2008; H01J 2237/201; G01N 23/225; G01N 1/286; G01N 23/2204; G01N 23/2251

USPC ................... 250/440.11; 73/864.91
See application file for complete search history.

(56) References Cited

U.S. PATENT DOCUMENTS

| 5,440,123 | A | * | 8/1995 | Ikeda | 250/307 |
| 5,572,026 | A | * | 11/1996 | Ikeda | 250/307 |
| 7,115,882 | B2 | | 10/2006 | Moore | |
| 7,126,132 | B2 | | 10/2006 | Moore | |
| 7,126,133 | B2 | | 10/2006 | Moore | |

(Continued)

FOREIGN PATENT DOCUMENTS

DE 102009001587 7/2010

OTHER PUBLICATIONS

Unknown, 'FIB Lift-Out Grids and Grid Boxes,' http://www.tedpella.com/grids_html/4510half.htm, 4 pages, obtained Jan. 14, 2014.

(Continued)

*Primary Examiner* — Jack Berman
*Assistant Examiner* — Wyatt Stoffa
(74) *Attorney, Agent, or Firm* — Scheinberg & Associates, PC; Michael O. Scheinberg; John E. Hillert

(57) ABSTRACT

The invention relates to a sample carrier for a transmission electron microscope. When using state of the art sample carriers, such as half-moon grids in combination with detectors detecting, for example, X-rays emitted at a large emittance angle, shadowing is a problem. Similar problems occur when performing tomography, in which the sample is rotated over a large angle.
The invention provides a solution to shadowing by forming the parts of the grid bordering the interface between sample and grid as tapering parts.

19 Claims, 2 Drawing Sheets

(56) References Cited

U.S. PATENT DOCUMENTS

Figure 1A:
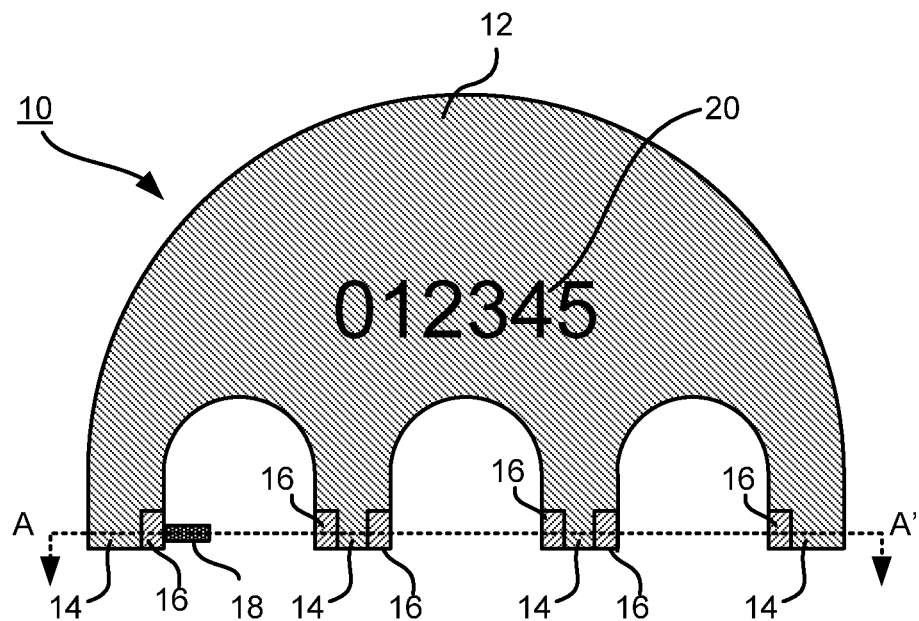

| | | | |
|---|---|---|---|
| 7,315,023 | B2 | 1/2008 | Moore |
| 7,767,979 | B2 | 8/2010 | Dona |
| 8,011,259 | B2 | 9/2011 | Dona |
| 8,080,791 | B2 | 12/2011 | Von Harrach et al. |
| D657,474 | S | 4/2012 | Dona |
| 8,389,955 | B2* | 3/2013 | Lehmann ................. 250/440.11 |
| 8,410,439 | B2 | 4/2013 | Von Harrach et al. |
| 8,592,764 | B2 | 11/2013 | Von Harrach et al. |
| 2006/0189021 | A1* | 8/2006 | Iwasaki et al. ................. 438/48 |
| 2008/0185286 | A1* | 8/2008 | Lehmann ................. 204/192.34 |
| 2010/0230584 | A1 | 9/2010 | Niebel et al. |
| 2010/0243888 | A1* | 9/2010 | Nishiyama et al. ........... 250/307 |
| 2011/0006208 | A1* | 1/2011 | Freitag et al. ................ 250/307 |
| 2011/0097706 | A1* | 4/2011 | Van Veen et al. ................. 435/5 |
| 2011/0284745 | A1* | 11/2011 | Nishiyama et al. ........... 250/307 |
| 2012/0120226 | A1* | 5/2012 | De Jonge ........................ 348/80 |
| 2012/0189813 | A1* | 7/2012 | Lechner et al. ............... 428/156 |
| 2012/0298883 | A1* | 11/2012 | Grogan et al. ........... 250/440.11 |
| 2013/0328246 | A1* | 12/2013 | Wells et al. ................... 264/400 |

OTHER PUBLICATIONS

Unknown, 'PELCO Silicon Aperture Frames (without support film),' http://www.tedpella.com/grids_html/silicon-aperture.htm, 2 pages, obtained Jan. 14, 2014.

Unknown, 'PELCO, Silicon Nitride Support Films for TEM,' in http://www.tedpella.com/grids_html/silicon-nitride-details.htm, 5 pages, obtained Jan. 14, 2014.

* cited by examiner

SAMPLE CARRIER FOR AN ELECTRON MICROSCOPE

This Application claims priority from U.S. Provisional Application 61/752,514, filed Jan. 15, 2013, which is hereby incorporated by reference.

The invention relates to a sample carrier for an electron microscope, the sample carrier comprising a metal foil, the sample carrier comprising at least one mounting position bordering a lateral side of the metal foil for attaching a sample thereto.

The invention further relates to a method of using such a sample carrier.

Such a sample carrier is available from Ted Pella Inc., Redding, Calif., USA, under the name Lift-Out Grid (e.g., product number 460-224).

The known lift-out grid resembles a half-circle with a diameter of 3 mm and is formed from a 25-30 µm thick molybdenum foil. On the straight edge of the half-circle it shows four protruding teeth, the ends of the teeth intended to be used as mounting position for samples. The grid thus shows multiple mounting positions. The grid is relatively stiff, making the sample carrier resilient to vibration, buckling, etc.

It is noted that a high stiffness and the resulting resilience to vibration are necessary for making images at a high resolution, for example at a resolution of less than 1 nm as used in a Scanning Electron Microscope (SEM) or even less than 0.1 nm as used in a Transmission Electron Microscope (TEM).

The process of excavating a sample from a work-piece and attaching the excavated sample to a grid is known from e.g. MAYER, Joachim et al, 'TEM Sample preparation and FIB-induced damage', MRS Bulletin Vol. 32, May 2007, p. 400-407, more specifically page 401: 'In-situ Lift-out/microsampling'.

MAYER describes how a sample is in situ excavated from a wafer, thinned and attached to a grid in a Focused Ion Beam (FIB) machine. Alternatively the sample is excavated, then attached to the grid and finally thinned.

It is noted that a thinned sample is often named a lamella. In this application the phrases 'lamella' and 'sample' are therefore used interchangeable.

The resulting lamella is thinned to be transparent to electrons and has a typical thickness of 50 nm or less. The area of the lamella is typically a rectangle with sides of several micrometers to several tens of micrometers large, for example a rectangle with a dimension of 5 µm×15 µm.

After preparing the lamella and attaching the lamella to the lift-out grid the lift-out grid is then transferred from the Focused Ion Beam machine to a TEM. In a TEM the lamella is irradiated with a beam of electrons with an energy of, for example, 300 keV, in response to which radiation is emitted. This radiation includes transmitted electrons, reflected electrons, secondary electrons, X-rays, etc.

From the electrons, their scattering and/or energy loss an image can be formed of the lamella.

The X-rays can be used to form an image providing elemental information of the sample, based on the characteristic X-rays emitted from the lamella. To that end a focused beam of electrons is scanned over the lamella and detectors detect the emitted X-rays. For optimum processing speed the detectors are placed to surround the sample so that X-rays emitted from as large an emittance solid angle as possible are detected. This is described in, for example, U.S. Pat. No. 8,080,791 B2.

A problem of the known lift-out grid is that, when the sample is welded to the grid, a large part of the emittance solid angle is blocked by the grid, especially near the sample/grid interface. As a result a large fraction of the X-rays cannot be detected, resulting in longer processing times and/or wrong evaluation of the amount of X-rays emitted from the sample. It is noted that the sample is typically only a few µm long, and the foil typically 25 µm thick, resulting in a large shadowing effect, shadowing almost 50% of the emittance solid angle of the X-rays.

A similar problem arises when an X-ray or e-beam tomogram is made, in which the sample is rotated (tilted) over an axis perpendicular to the beam of electrons and at a large number of said tilt angles an image is made. These images at different tilt angles are then used to reconstruct a 3D image of the sample. It is noted that for a tomogram often thicker samples, with a thickness between 70 nm and 1 µm (depending on sample composition) are used.

As part of the sample is shadowed by the grid (either downstream of the beam of electrons or upstream), the tomogram is limited to tilt angles where the sample is not or hardly obscured. Also the shadowing depends on the tilt angle used. The 3D reconstruction is thus limited in resolution (as only a wedge of the tilt angles that are mechanically possible result in a useful detected signal), especially for the part of the sample near the grid/sample interface.

The invention intends to provide a solution to these problems.

To that end the sample carrier according to the invention is characterized in that the mounting position borders a part of the sample carrier in which the thickness of the metal foil is reduced.

By reducing the thickness of the sample carrier locally, and attach the sample to a part with reduced thickness, the shadowing of the radiation resulting from the sample carrier is reduced.

It is noted that it is known to attach a sample to a needle instead of to a grid. This is described in U.S. Pat. No. 7,115,882 B2. This patent describes that a sample is in a FIB excavated from a work piece and attached to a sharp needle. The sharp needle is then taken out of the FIB and, using a pneumatic press, ex-situ pressed in a copper ring. The copper ring with the sharp needle and the sample are then re-introduced into the FIB for thinning the sample to electron transparency. After thinning the thinned sample can then be introduced in a TEM for further inspection.

A disadvantage of this method is that, due to the necessity of pressing the needle in the copper with a pneumatic press, this must be done outside the FIB and involves several steps, such as inserting the copper ring in the press, inserting and positioning the needle in the press, etc. This lowers throughput and decreases user-friendliness, and increases the risk of accidental detachment of the sample from the needle, with associated loss of the sample. Further the sample is effectively mounted at the end of a needle, and is thus prone to vibrations. Another disadvantage is that the sample is mounted perpendicular to the needle, the needle attached to the middle of the sample. Thinning necessarily takes place on one or both wings (the distal parts of the sample as seen from the point of attachment). For identical sample sizes these wings and thus the continuous areas of interest wherein a structure of interest may reside are thus smaller. As known to the person skilled in the art this is very unfavorable, as a feature, such as a transistor, should be in one continuous area. Also, as the needle is on average closer, the background level of needle material is higher.

Therefore the use of such a sample holder and its associated use are not preferred when looking for a method resulting in high-throughput and the low vibration levels necessary for high-resolution imaging.

It is further noted that it may be contemplated to form the sample holder from a crystalline material and then shape the sample carrier by preferential etching, as done for example for the Silicon Aperture Frames available from Ted Pella Inc. (e.g., product number 21545-10). However, the resulting angle of (90–35.26) degrees—thus: 54.74 degrees—is less than optimal, as still a large solid angle is blocked.

In an embodiment of the invention the reduced thickness of the metal foil is achieved by a tapering of the foil.

In another embodiment of the sample carrier according to the invention the metal foil has a thickness of at least 20 μm and the part with a reduced thickness has a thickness of at most 10 μm.

Preferably the metal is Mo, Ti. Be or Cu.

The object of the inspection of the sample is often to observe whether a given element is present in the sample at a given location, or not. The sample carrier often gives rise to a background signal. Further it is preferred when the material of the sample carrier absorbs as little X-rays emitted by the sample as possible. This makes beryllium the material of choice. However, its toxicity and difficulty of machining makes it expensive and unfit for normal use. Mo and Ti are well machinable, and are fit for normal use. Cu is preferred for low-cost applications.

A preferred method of forming the taper in metal foil is using laser ablation. Although other methods may be used, they often show disadvantages (for example: stamping results in standing edges).

To achieve a large acceptance solid angle for the detectors a taper angle of the tapering with respect to the flat of the sample carrier of less than 45 degrees, more specifically less than 30 degrees, most specifically less than 20 degrees should be realized.

It is noted that for a price competitive product the sample carrier is preferable from one material only. However, for easy maneuvering of the sample on the sample carrier it may be preferred to add a carbon foil to the sample carrier as described in U.S. patent application publication no. U.S. 2008/0185286 A1.

In an aspect of the invention a method of preparing a sample for inspection in an electron microscope, the method comprising the steps of:
  in an evacuated sample chamber of an apparatus equipped with a Focused Ion Beam column excavating a sample from a work piece and welding the sample to a mounting position of a sample carrier, the sample carrier formed from a metal foil,
  while keeping the sample in the evacuated chamber of the apparatus thin the sample to form a lamella, and
  inspecting the thus formed lamella with an electron beam,
is characterized in that
  the mounting position of the sample carrier borders a part of the sample carrier in which the thickness of the metal foil is reduced Typically excavating a sample from a work piece is done in the evacuated sample chamber of an apparatus equipped with a Focused Ion Beam column. The focused ion beam can remove material by sputtering and/or gas assisted etching. For this the work piece is placed in a sample chamber of the FIB, and irradiated with the focused ion beam. When the sample is excavated from the work piece, it is attached (welded, glued) to the sample carrier according to the invention and thinned to a lamella. After that it is introduced in a TEM for further inspection.

It is noted that compared to the earlier described method described in U.S. patent publication no. U.S. Pat. No. 7,115,882 B2, where outside the vacuum the sample is welded to a needle, and the needle is pressed in a copper ring, a marked time reduction is achieved, as a vent-pump cycle of the apparatus is eliminated. Also the risk of losing the sample is reduced.

In an embodiment of the method the inspection with an electron beam comprises acquiring a tomogram.

In an embodiment of the method the inspection with an electron beam comprises detecting of transmitted electrons and/or detecting X-rays.

It is noted that the inspection with an electron beam can take place in a TEM (typically using a selectable beam energy of between 60 keV and 300 keV) or a SEM (typically using a selectable beam energy of between 10 and 30 keV).

Figure 1B:
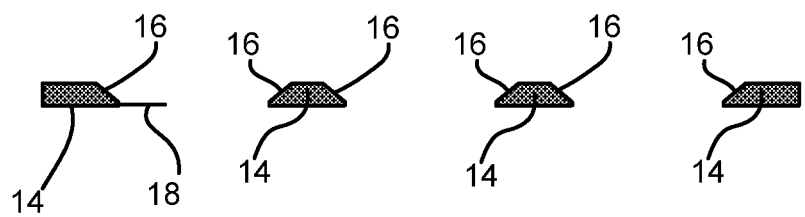
Figure 2:
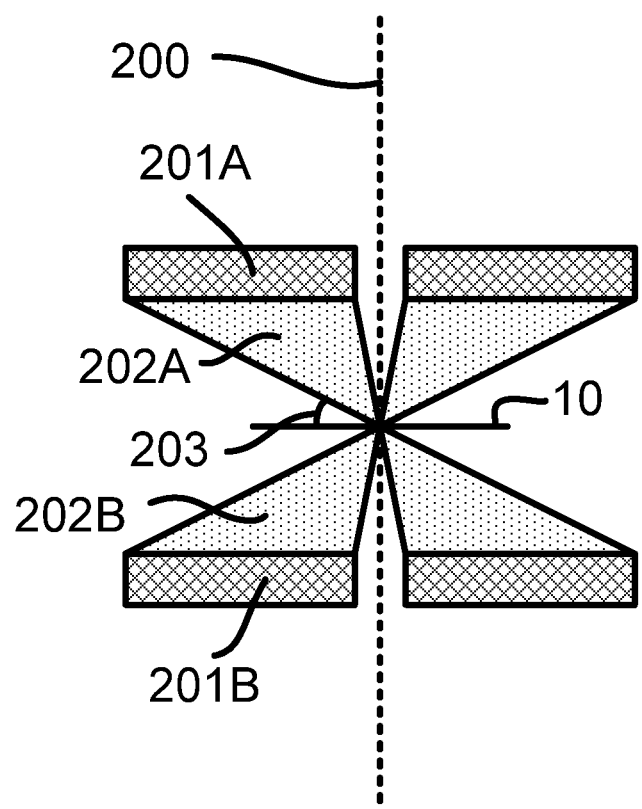

The invention is now elucidated using figures, in which identical numerals refer to corresponding features. To that end:

FIG. 1A schematically shows a top view of the sample carrier according to the invention;

FIG. 1B schematically shows a cross-section of the sample carrier of FIG. 1A along line AA'; and FIG. 2 schematically shows a sample carrier between detectors.

FIG. 1A schematically shows a top view of the sample carrier according to the invention.

FIG. 1A shows a sample carrier 10 comprising a metal foil 12. The sample carrier shows 4 teeth 14, each showing one or more sloping edges 16 towards mounting positions. A sample 18 is welded on one of these mounting positions. Optionally the sample carrier shows an identification mark 20 to discriminate one sample carrier from another.

The welding of the sample may be done by beam induced deposition (BID), more specifically ion beam induced deposition (IBID) or electron beam induced deposition (EBID), but also beam induced deposition using for example a laser beam can be used. Also other adhesive processes can be used.

FIG. 1B schematically shows a cross-section of the sample carrier of FIG. 1A along line AA'.

FIG. 1B shows a cross-section along the teeth of the sample carrier, line AA' of FIG. 1A. It shows the sloping edges 16 of the tapers of the teeth 14.

It is noted that the sample carrier 10 can be formed as a so-named half-moon grid, as shown in FIG. 1 but also sample carriers as known from e.g. U.S. Pat. No. 7,767,979 B2 can be modified with tapering edges to which the sample can be adhered to form a sample carrier according to the invention.

It is further noted that here a sample carrier is described with tapers at one side (the upper side or the lower side). The grid may show two tapering surface 16, resulting in a mounting part that does not coincides with one of the surfaces of the metal foil 12.

FIG. 2 schematically shows a sample carrier between detectors.

FIG. 2 shows a beam 200 of electrons, the electrons having a selectable energy of, for example, between 10 keV and 30 keV when used in a SEM and, for example, between 80 and 300 keV when used in a TEM. The beam impinges on a sample mounted on a sample carrier 10, as a result of which X-rays are emitted. The X-rays are detected by two detectors 201A and 201B. The detectors are preferably circular in form with a central hole for passing the beam of electrons. As a result all X-rays in solid angles 202A and 202B are detected.

It is presumed that the angle 203, defining the angle to the outermost part of the detector, coincides with the angle of the sloping edges 16, so that no or little shadowing occurs.

I claim:

1. A sample carrier for carrying a sample in an electron microscope, the sample carrier comprising a metal foil, the sample carrier comprising at least one mounting position on a lateral side of a tapered portion of the metal foil for attaching a sample thereto, wherein the at least one mounting position borders a part of the sample carrier in which a thickness of the metal foil is reduced, wherein the part comprises the tapered portion, and wherein the lateral side of the metal foil is substantially not parallel to a flat of the sample carrier.

2. The sample carrier of claim 1 in which the metal foil has a thickness of at least 20 µm and the part with a reduced thickness has a thickness of at most 10 µm.

3. The sample carrier of claim 1 in which the metal is Mo, Ti, Be or Cu.

4. The sample carrier of claim 1 in which the tapered portion shows a taper angle with respect to the flat of the sample carrier of less than 45 degrees.

5. The sample carrier of claim 4 in which the taper angle is less than 30 degrees.

6. The sample carrier of claim 5 in which the taper angle is less than 20 degrees.

7. The sample carrier of claim 1 in which the tapered portion is formed by laser ablation of the metal.

8. The sample carrier of claim 1 in which the sample carrier has a uniform consistency.

9. The sample carrier of claim 1 in which the sample carrier comprises a carbon foil extending beyond the boundaries of the metal foil.

10. The sample carrier of claim 1 in which the metal foil has a thickness of at least 20 µm and the part with a reduced thickness has a thickness of at most 10 µm.

11. The sample carrier of claim 2 in which the tapered portion is formed by laser ablation of the metal.

12. The sample carrier of claim 3 in which the tapered portion is formed by laser ablation of the metal.

13. The sample carrier of claim 4 in which the tapered portion is is formed by laser ablation of the metal.

14. The sample carrier of claim 1 in which the sample carrier has a uniform consistency.

15. The sample carrier of claim 1 in which the sample carrier comprises a carbon foil extending beyond the boundaries of the metal foil.

16. A method of preparing a sample for inspection in an electron microscope, the method comprising:

in an evacuated sample chamber of an apparatus equipped with a focused ion beam column, excavating a sample from a work piece and welding the sample to a sample carrier;

thinning the sample to form a lamella while keeping the sample in the evacuated sample chamber of the apparatus; and inspecting the thus formed lamella with an electron beam, wherein:

from the moment that the sample is excavated from the work piece until at least the moment that the sample is thinned to a lamella, the sample is kept in the evacuated sample chamber of the apparatus, and the sample carrier is a sample carrier for carrying a sample in an electron microscope comprising a metal foil and at least one mounting position on a lateral side of a tapered portion of the metal foil for attaching a sample thereto, wherein the at least one mounting position borders a part of the sample carrier in which a thickness of the metal foil is reduced, wherein the part comprises the tapered portion, and wherein the lateral side of the metal foil is substantially not parallel to a flat of the sample carrier.

17. The method of claim 16 in which inspecting the thus formed lamella with an electron beam comprises acquiring a tomogram.

18. The method of claim 17 in which inspecting the thus formed lamella with an electron beam comprises detecting transmitted electrons and/or detecting X-rays.

19. The method of claim 16 in which inspecting the thus formed lamella with an electron beam comprises detecting transmitted electrons and/or detecting X-rays.

* * * * *